(12) United States Patent
Consigny et al.

(10) Patent No.: US 9,636,486 B2
(45) Date of Patent: May 2, 2017

(54) METHODS AND DEVICES FOR ELUTING AGENTS TO A VESSEL

(71) Applicant: Abbott Cardiovascular Systems Inc., Santa Clara, CA (US)

(72) Inventors: Paul M. Consigny, San Jose, CA (US); William E. Webler, San Jose, CA (US); Gustavo D. Cipolla, San Francisco, CA (US); Gordon S. Stewart, San Ramon, CA (US); Benjamyn Serna, Gilroy, CA (US); Daniel L. Cox, Palo Alto, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

(21) Appl. No.: 14/952,811

(22) Filed: Nov. 25, 2015

(65) Prior Publication Data

US 2016/0074635 A1 Mar. 17, 2016

Related U.S. Application Data

(62) Division of application No. 14/053,456, filed on Oct. 14, 2013, now Pat. No. 9,216,027, which is a division
(Continued)

(51) Int. Cl.
*A61M 25/10* (2013.01)
*A61B 17/22* (2006.01)
*A61M 25/00* (2006.01)

(52) U.S. Cl.
CPC .......... *A61M 25/104* (2013.01); *A61B 17/22* (2013.01); *A61M 25/10* (2013.01);
(Continued)

(58) Field of Classification Search
CPC .... A61M 2025/1081; A61M 2025/105; A61M 25/10; A61M 25/104; A61M 2025/0057;
(Continued)

(56) References Cited

U.S. PATENT DOCUMENTS 4,437,856 A 3/1984 Valli
4,693,243 A 9/1987 Buras
(Continued)

FOREIGN PATENT DOCUMENTS

EP 0511499 3/1992
EP 0567788 3/1993
(Continued)

OTHER PUBLICATIONS

Abbot Cardiovascular Systems, Non-Final Office Action mailed Dec. 18, 2013 for U.S. Appl. No. 14/053,456.
(Continued)

*Primary Examiner* — Theodore Stigell
(74) *Attorney, Agent, or Firm* — Blakely Sokoloff Taylor & Zafman; William Thomas Babbitt

(57) ABSTRACT

Systems, devices and methods for eluting an agent at a treatment site are disclosed. The devices include an expandable frame and at least one membrane. The membrane may carry an agent to elute at the treatment site. The membrane may allow blood flow at the treatment site during agent delivery.

5 Claims, 12 Drawing Sheets

Related U.S. Application Data of application No. 13/349,499, filed on Jan. 12, 2012, now Pat. No. 8,556,849, which is a division of application No. 11/901,575, filed on Sep. 17, 2007, now Pat. No. 8,100,855.

(52) U.S. Cl.
CPC ............ *A61B 2017/22042* (2013.01); *A61B 2017/22051* (2013.01); *A61B 2017/22084* (2013.01); *A61M 2025/0057* (2013.01); *A61M 2025/105* (2013.01); *A61M 2025/1081* (2013.01)

(58) Field of Classification Search
CPC .......... A61B 17/22; A61B 2017/22042; A61B 2017/22084; A61B 2017/22051
USPC ...................................... 604/96.01, 105–106
See application file for complete search history.

(56) References Cited

U.S. PATENT DOCUMENTS

| | | | |
|---|---|---|---|
| 5,188,602 A | | 2/1993 | Nichols |
| 5,207,644 A | * | 5/1993 | Strecker ............ A61M 39/0208 604/164.01 |
| 5,250,070 A | | 10/1993 | Parodi |
| 5,304,121 A | | 4/1994 | Sahatjian |
| 5,389,106 A | | 2/1995 | Tower |
| 5,498,238 A | | 3/1996 | Shapland et al. |
| 5,558,642 A | | 9/1996 | Schweich et al. |
| 5,709,874 A | | 1/1998 | Hanson et al. |
| 5,713,860 A | | 2/1998 | Kaplan et al. |
| 5,741,333 A | | 4/1998 | Frid |
| 5,800,392 A | | 9/1998 | Racchini |
| 5,810,767 A | | 9/1998 | Klein |
| 5,863,284 A | | 1/1999 | Klein |
| 5,971,968 A | | 10/1999 | Tu et al. |
| 6,053,932 A | * | 4/2000 | Daniel ............ A61B 17/22031 604/104 |
| 6,068,611 A | | 5/2000 | Loffler et al. |
| 6,263,236 B1 | | 7/2001 | Kasinkas et al. |
| 6,540,721 B1 | | 4/2003 | Voyles et al. |
| 6,551,341 B2 | | 4/2003 | Boylan et al. |
| 6,623,452 B2 | | 9/2003 | Chien et al. |
| 6,645,135 B1 | | 11/2003 | Bhat |
| 6,695,813 B1 | | 2/2004 | Boyle et al. |
| 6,709,427 B1 | | 3/2004 | Nash et al. |
| 6,821,242 B1 | | 11/2004 | Waksman et al. |
| 6,899,729 B1 | | 5/2005 | Cox et al. |
| 6,913,612 B2 | | 7/2005 | Palmer et al. |
| 6,939,376 B2 | | 9/2005 | Shulze et al. |
| 8,100,855 B2 | | 1/2012 | Consigny et al. |
| 8,556,849 B2 | | 10/2013 | Consigny et al. |
| 2001/0014717 A1 | | 8/2001 | Hossainy et al. |
| 2001/0044647 A1 | | 11/2001 | Pinchuk et al. |
| 2002/0007209 A1 | | 1/2002 | Scheerder et al. |
| 2002/0007215 A1 | | 1/2002 | Falotico et al. |
| 2002/0051730 A1 | | 5/2002 | Bodnar et al. |
| 2002/0090388 A1 | | 7/2002 | Humes et al. |
| 2002/0143385 A1 | | 10/2002 | Yang |
| 2003/0100886 A1 | | 5/2003 | Segal et al. |
| 2004/0236412 A1 | | 11/2004 | Brar et al. |
| 2005/0015129 A1 | | 1/2005 | Mische |
| 2005/0113907 A1 | | 5/2005 | Fischell |
| 2005/0175666 A1 | | 8/2005 | Ding |
| 2006/0020331 A1 | * | 1/2006 | Bates ...................... A61F 2/82 623/1.49 |
| 2006/0271098 A1 | | 11/2006 | Peacock |
| 2009/0069789 A1 | | 3/2009 | Freyman et al. |

FOREIGN PATENT DOCUMENTS

| | | |
|---|---|---|
| EP | 0712615 | 5/1996 |
| EP | 0819011 | 3/2003 |
| EP | 1637084 | 3/2006 |
| WO | WO-9716170 | 5/1997 |
| WO | WO-9742998 | 11/1997 |
| WO | WO-0226139 | 4/2002 |
| WO | WO-0226281 | 4/2002 |
| WO | WO-0249706 | 6/2002 |
| WO | WO-03039612 | 5/2003 |
| WO | WO-2007002750 | 1/2007 |
| WO | WO-2007089897 | 8/2007 |

OTHER PUBLICATIONS

Abbot Cardiovascular Systems, Final Office Action mailed Sep. 24, 2014 for U.S. Appl. No. 14/053,456.
Abbott Cardiovascular Systems, Non-Final Office Action mailed Dec. 22, 2014 for U.S. Appl. No. 14/053,456.
Abbott Cardiovascular Systems, Final Office Action mailed Jun. 18, 2015 for U.S. Appl. No. 14/053,456.
Abbott Cardiovascular Systems, Non final office action mailed Jun. 19, 2014 for U.S. Appl. No. 14/053,456.
Abbott Cardiovascular Systems, Final office action mailed May 6, 2013 for U.S. Appl. No. 13/349,499.
Abbott Cardiovascular Systems, Final office action dated Apr. 19, 2010 for U.S. Appl. No. 11/901,575.
Abbott Cardiovascular Systems, PCT International search report and written opinion dated Jan. 15, 2009 for PCT/US2008/008913.
Abbott Cardiovascular Systems, Invitation to pay additional fees dated Nov. 18, 2008 for PCT/US2008/008913.
Abbott Cardiovascular Systems, International Preliminary Report on Patentability dated Apr. 1, 2010 for PCT/US2008/008913.
Abbott Cardiovascular Systems, Non final office action dated Aug. 6, 2009 for U.S. Appl. No. 11/901,575.
Abbott Cardiovascular Systems, Non final office action mailed Sep. 13, 2010 for U.S. Appl. No. 11/901,575.
Abbott Cardiovascular Systems, Final Office Action mailed Jan. 27, 2011 for U.S. Appl. No. 11/901,575.
Abbott Cardiovascular Systems, Non-Final Office Action dated Oct. 1, 2012 for U.S. Appl. No. 13/349,499.
Mitchel, J. F., et al., "Enhanced intracoronary thrombolysis with urokinase using a novel, local drug delivery system", Circulation, 91, (1995), 785-793.
Moura, A., et al., "Intramural delivery of agent via a novel drug delivery sleeve", Circulation, 92, (1995), 2299-2305.
O, Tahlil, et al., "The dispatch catheter as a delivery tool for arterial gene transfer", Cardiovascular Research, 33(1), (1977), 181-187.

\* cited by examiner

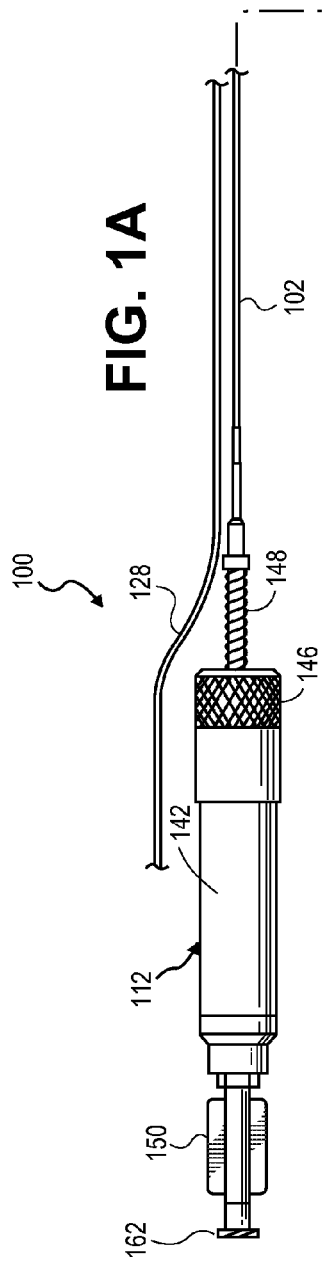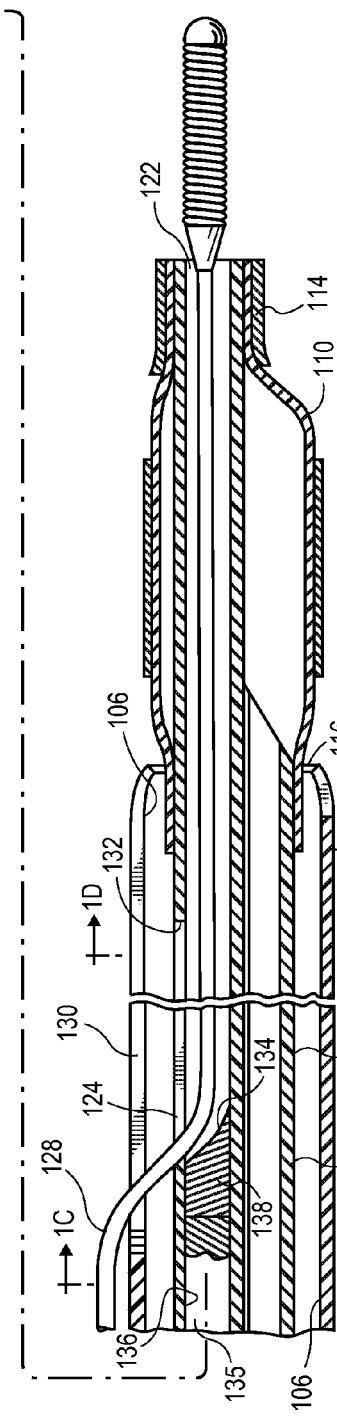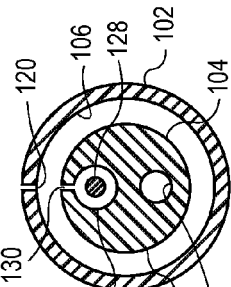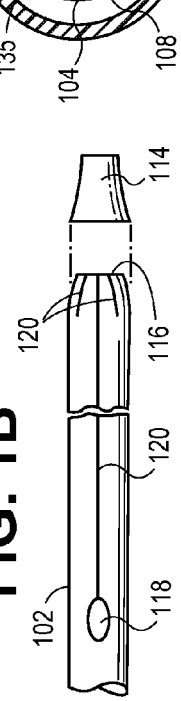

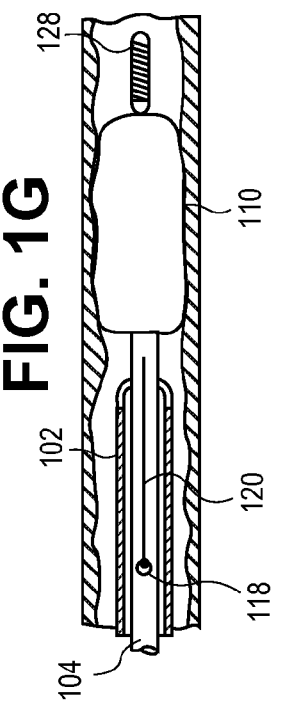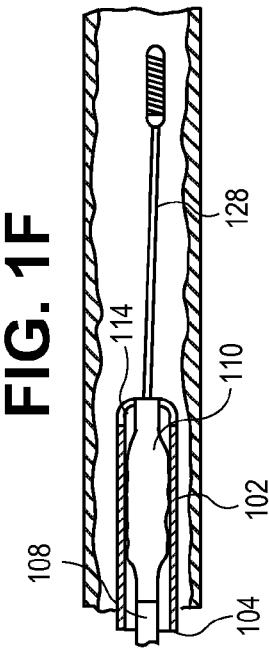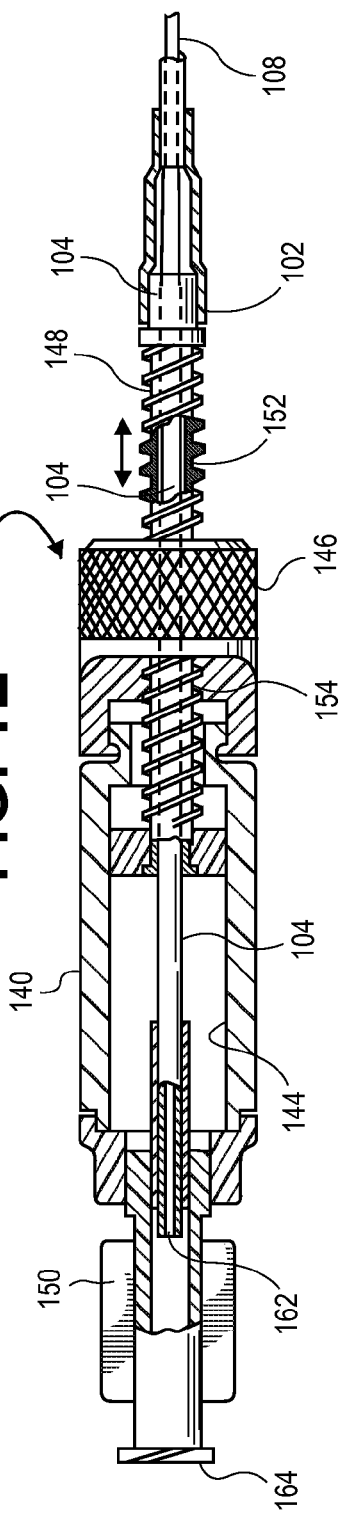

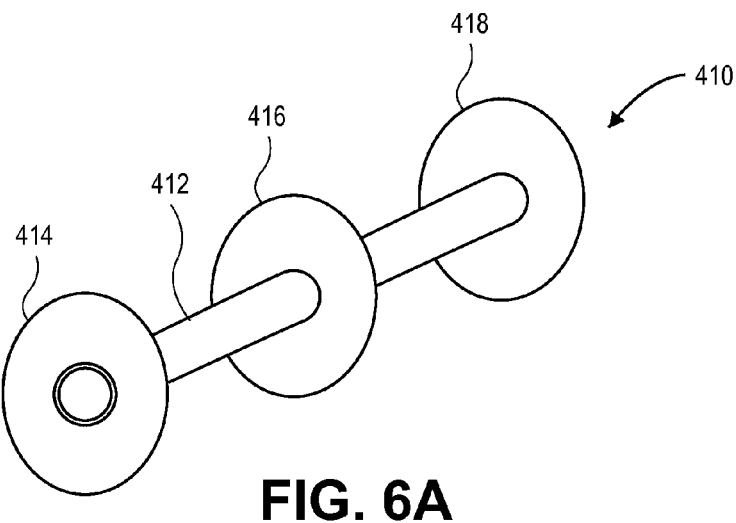
FIG. 6A
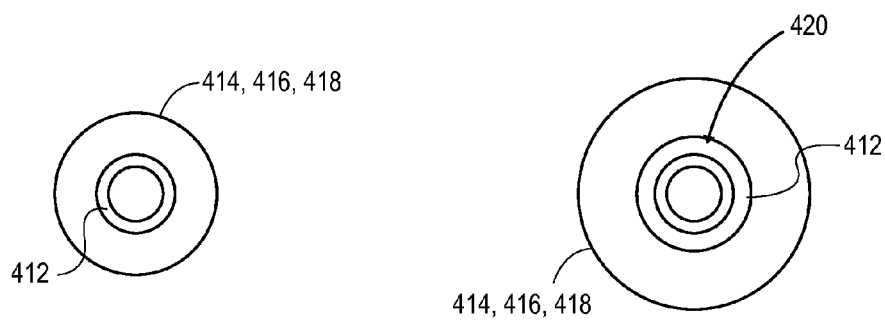
FIG. 6B  FIG. 6C
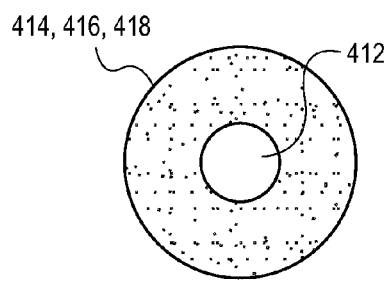   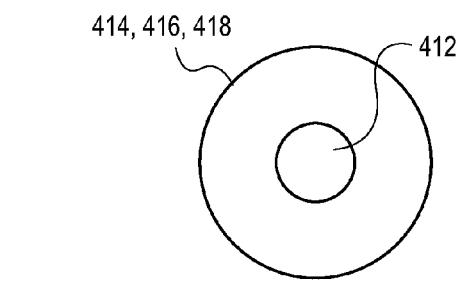
FIG. 6D  FIG. 6E

METHODS AND DEVICES FOR ELUTING AGENTS TO A VESSEL

CROSS-REFERENCE TO RELATED APPLICATIONS

The application is a divisional of co-pending U.S. patent application Ser. No. 14/053,456, filed Oct. 14, 2013, which is a divisional of co-pending U.S. patent application Ser. No. 13/349,499, filed Jan. 12, 2012 (issued as U.S. Pat. No. 8,556,849), which is a divisional of co-pending U.S. patent application Ser. No. 11/901,575, filed Sep. 17, 2007 (issued as U.S. Pat. No. 8,100,855) and incorporated herein by reference.

FIELD

The present invention relates generally to medical devices, and more particularly to an assembly for delivery of an agent to a vessel.

BACKGROUND

In the treatment of diseased vasculature, therapeutic agents have commonly been administered, typically as part of other interventional therapies such as angioplasty or stent delivery. Local, as opposed to systemic delivery, is a preferred method of treatment in that smaller total levels of medication are administered in comparison to systemic dosages, yet are concentrated at a specific site. As a result, local delivery produces fewer side effects and achieves more effective results.

A variety of methods and devices have been proposed for percutaneous drug delivery to a diseased region of the vasculature. For example, catheters having porous balloons can be used to deliver a therapeutic agent infused into the inflatable interior of the porous balloon and through the porous wall of the balloon. Alternatively, prostheses such as stents or other implantable devices provide for local drug delivery when coated or otherwise made to include a therapeutic agent which elutes from the implanted prosthesis. Another suggested method involves the use of one or more catheters having multiple balloons. The diseased region is isolated by inflating the balloons on either side of the diseased region, and the therapeutic agent is infused through a lumen of the catheter shaft and into the isolated diseased region from a delivery port on the catheter shaft located between the balloons.

One disadvantage with using a balloon to deliver drugs is that the balloons typically have a plain surface and therefore the contact to the artery wall is uniform and the whole endothelium receives the pressure of the balloon surface. Such contact causes endothelial damage/injury during the particular drug delivery procedure. Endothelial denudation (a loss of a surface layer) is associated with or representative of the endothelial damage caused by the balloon wall contact.

Another difficulty has been maximizing the amount of drug taken-up and retained at the diseased site, while minimizing the washout of large amounts of drug downstream of the treatment site. Drug washout reduces the efficiency of local intravascular drug delivery, in addition to causing potentially harmful systemic exposure to the drug. Therefore, it would be a significant advance to provide an improved device and method for providing therapy to a desired location within a patient's body lumen. Another difficulty with using a balloon is the limited treatment time resulting from ischemia.

SUMMARY

In one embodiment, an agent delivery device having a guide wire having a proximal end and a distal end; and an expandable device at the distal end of the guide wire, the expandable device having two or more expandable, elliptical wire loops adapted to contact an arterial wall and a polymeric membrane having an elutable agent attached to the two or more expandable, elliptical wire loops between ends of the loops adapted to protect the luminal surface of the vessel from elevated shear stress and to carry the elutable agent into the arterial wall while the polymeric membrane is in contact with the luminal surface of the artery is disclosed.

In one embodiment, an agent delivery device having a self-expanding device, the device having a proximal portion, a distal portion, and a central portion between the proximal portion and the distal portion, the proximal portion and the distal portion configured to apply a greater pressure to a vessel wall than the central portion and adapted to form a seal with the vessel wall at a proximal end and a distal end of the self-expanding device; and a substantially impermeable membrane covering the device is disclosed.

The device may also include a catheter or guidewire, the self-expanding device being mounted on the catheter or guidewire. The self-expanding device may be retractable.

The proximal portion may include a proximal seal and the distal portion may include a distal seal. The proximal portion may include a proximal ring and the distal portion may include a distal ring. The proximal portion and the distal portion may incorporate more metal than the central portion of the self-expanding device to form the proximal ring and distal ring, respectively. The expanded diameter of the proximal portion and the expanded diameter of the distal portion may be greater than the expanded diameter of the central portion of the self-expanding device.

The membrane may not cover the proximal end or the distal end. The membrane may be a first membrane and the device may also include a second, porous membrane covering the first membrane, the first membrane being less porous than the second membrane. The device may include an inner member having an infusion lumen therein. A distal end of the infusion lumen may be attached and sealed to the self-expanding device such that the infusion lumen communicates with an area between the first membrane and the second membrane. The infusion lumen may be configured to deliver an agent. The self-expanding device may include a lumen extending from the proximal end to the distal end. The lumen may be a perfusion lumen.

In one embodiment, an agent delivery device having an expandable device including a plurality of tubular members, the tubular members having openings therein to deliver an agent, the expandable device having an inner surface and an outer surface; and a substantially impermeable membrane at the inner surface of the expandable device is disclosed.

The device may also include a manifold at a distal end of the expandable device, the tubular members fluidly coupled with the manifold. The manifold may be connected to a port that delivers an agent to the tubular members. The plurality of tubular members may be arranged to form an expandable frame. The device may include a flap over a portion of the outer surface of the expandable device adapted to enclose a space between the membrane and a vessel wall.

In one embodiment, an agent delivery device having a plurality of tubular members, each tubular member having a port and a plurality of openings configured to deliver an agent to a vessel wall; an inflation lumen connected to the port of each of the tubular members to deliver the agent to the plurality of tubular members; and a substantially impermeable membrane attached to an inner surface of the plurality of tubular members, the substantially impermeable membrane to isolate the agent from blood flow in the vessel is disclosed.

In one embodiment, an agent delivery device having an expandable device having a spring; an elastic balloon surrounding the spring; an agent coating the balloon; and a retractable sheath surrounding the balloon and expandable device having a retracted position and an unretracted position, wherein the spring expands when the sheath is in the retracted position and the agent is protected in the unretracted position is disclosed. The spring may be nitinol. The spring may be retractable. The drug may be coated on the elastic balloon in stripes.

In one embodiment an agent delivery device having a catheter; a spring in the catheter; an agent coating the catheter; and a retractable sheath surrounding the catheter and spring, wherein the spring expands when the sheath is retracted and wherein the sheath protects the agent is disclosed. The spring may be nitinol. The spring may be retractable.

The agent may be agents that inhibit intimal thickening, agents that inhibit pannus formation, agents that promote thrombus dissolution, thrombolytics, agents that inhibit local inflammation, agents that inhibit infection, anti-inflammatories, antibiotics, antirestenotics, and combinations thereof.

BRIEF DESCRIPTION OF THE DRAWINGS

The invention is described by way of example with reference to the accompanying drawings, wherein:

FIGS. 1A-G are schematic drawings of an exemplary delivery system in accordance with one embodiment of the invention;

FIGS. 6A-6E are side views of an elution device in accordance with one embodiment of the invention;

DETAILED DESCRIPTION

Figure 2A:
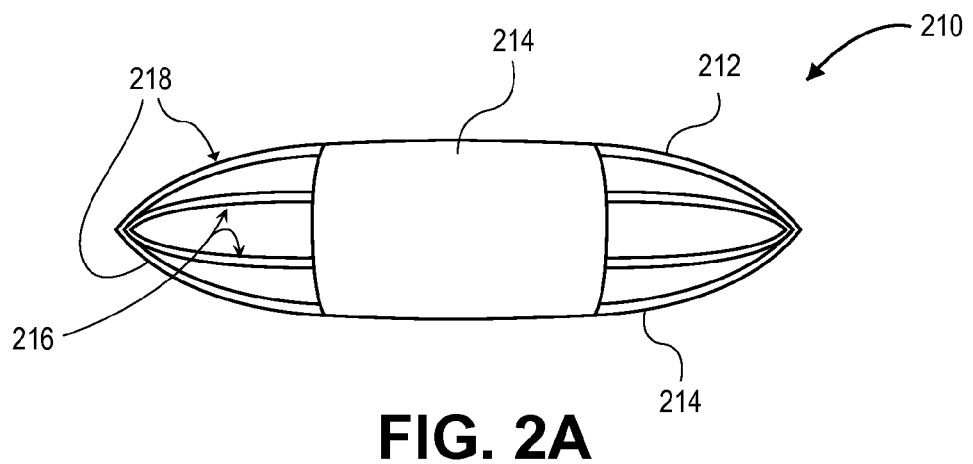
FIGS. 2A-2B are side views of an elution device in accordance with one embodiment of the invention.

Exemplary embodiments of the present invention relate to devices for eluting an agent at a treatment site. Exemplary embodiments of the present invention also relate to devices that allow agent elution for extended periods of time by, for example, allowing blood flow at the treatment site, and, in some embodiments, through side branches at or near the treatment site. Exemplary embodiments of the present invention also relate to devices for eluting an agent at a treatment site while reducing damage to the treatment site.

In the following description, for purposes of explanation, numerous specific details are set forth in order to provide a through understanding of the present invention. It will be evident, however, to one skilled in the art, that the present invention may be practiced without these specific details. In other instances, specific apparatus structures and methods have not been described so as not to obscure the present invention. The following description and drawings are illustrative of the invention and are not to be construed as limiting the invention.

As shown in FIGS. 1A-1G of the accompanying drawings, an exemplary delivery system is described. It will be appreciated that other delivery systems may be used to deliver the devices disclosed herein and that existing improvements to the design described herein or other similar designs could also be incorporated. The delivery system described herein is but an example of a delivery system that can be adapted to deliver the devices to a treatment site.

In FIG. 1A, the catheter assembly 100 includes a delivery sheath 102 and an intravascular catheter 104. The delivery sheath 102 includes a lumen 106. The intravascular catheter 104 is disposed within the lumen 106 of the delivery sheath 102. The intravascular catheter 102 has an elongated catheter body 108. In one embodiment, as shown in FIG. 1A, a device 110 is located at a distal portion of the catheter body 108.

A manipulating device or proximal handle 112 is provided on the proximal end of the delivery system 100, which is employed to effect relative axial or longitudinal movement between the delivery sheath 102 and the intravascular catheter 104. During the advancement of the delivery system 100 through the patient's vascular system to the treatment area, the delivery sheath 102 may be tucked with an elastic cone 114. FIG. 1B shows the location of the elastic cone 114 after the relative axial positions of the sheath 102 and catheter 104 are adjusted to expose the device 110.

The delivery sheath 102 has a distal port 116 in its distal end which is in fluid communication with the outer lumen 106 and a proximal port 118 disposed proximally to the distal port 116. The distal portion of the delivery sheath 102 tapers down in a spherical-like manner so that the cross-sectional area is somewhat less in the distal region than the cross-sectional area of the rest of the delivery sheath. In one embodiment, a slit 120 extends from the proximal port 118 to a location just proximal to the distal port 116. In one embodiment, a plurality of slits 120 in the wall of the sheath 102 extend a distance from the distal port 116. As contemplated, the slit(s) 120 would facilitate in the relative axial position adjustment of the sheath 102 and the intravascular catheter 104.

The intravascular catheter 104 also has a distal port 122 and a proximal port 124. The ports 122 and 124 are in fluid communication with an inner lumen 126 extending within the distal portion of the catheter 104. The lumen 126 is adapted to slideably receive a guidewire 128 therein. In one embodiment, the device 110 is positioned on or forms part of the guidewire 128. In one embodiment, a slit 130 extends from the proximal port 124 to a location 132 proximal to the proximal end of the device 110. The proximal end of the inner lumen 126 may be provided with a ramp 134 to guide the proximal end of the guidewire 128 out of the proximal port 122 of the intravascular catheter 104. Additional lumen(s) 137, such as, for example, a perfusion lumen and/or an inflation lumen, may be provided in the catheter 104. Proximal to the proximal port 124, the catheter body 108 may include a stiffening member 135 disposed in another inner lumen 136 provided in the catheter body 108. As shown in the drawings, the inner lumen 136 and the inner lumen 126 may be the same lumen with a plug 138 separating the two lumens 126, 136. The ramp 134 is shown on the distal side of the plug 138 in FIG. 1A. It will be appreciated that the particular arrangement may vary from that shown and described.

As illustrated in FIGS. 1A and 1E, the manipulator 140 on the proximal end of the delivery system has a housing 142 with an interior chamber 144, a cap 146, an elongated drive member 148 and a Luer lock 150. The cap 146 is rotatably mounted onto the distal end of the housing 142. The elongated drive member 148 has threading on the exterior thereof and which is at least partially disposed within the interior chamber 144. The Luer lock 150 is fixed within the proximal end of the housing 142

The proximal end of the sheath 102 is secured to the distal end of the elongated drive member 148 which extends out of the distal end of the housing 142. As shown in more detail in FIG. 1E, the proximal end of the catheter body 108 passes through passageway 152 in the elongated drive member 148 and is fixed within the Luer lock 150 by suitable means such as, for example, adhesive. The cap 146 which is rotatably mounted onto the distal end of the housing 142 is provided with an inner threaded collar 154 adapted to threadably engage the threaded exterior of the elongated driving member. Rotation of the cap 146 moves the elongated drive member 148 axially to thereby effect relative axial movement between the sheath 102 and the intravascular catheter 104.

The guidewire 128 (or other guiding member) is shown extending across the treatment site of the artery in FIG. 1F. The proximal end of the guidewire 128, which extends out of the patient during the procedure, is inserted through the elastic cone 114 by threading the guidewire 128 into a small aperture 154 and out of a larger aperture 156 of the cone 114. The guidewire 128 is then inserted through the distal port 162 in the distal end of the intravascular catheter 104 and advanced proximally through the inner lumen 126 until the proximal end of the guidewire impacts the ramp 134 and is thereby directed through the proximal port 124.

The intravascular catheter 104 is preferably positioned within the lumen 106 of the delivery sheath 102 so that at least a significant portion of the proximal port 118 of the sheath 102 is in alignment with the proximal port 124 of the intravascular catheter 104. In this manner, proximal advancement of the guidewire 128 through the lumen 126 will also direct the proximal end of the guidewire out the proximal port 118 in the delivery sheath 102. The sheath 102 is then tucked within the elastic cone 114 by inserting the distal end of the sheath 102 into the proximal end and the large aperture 156 of the cone 114. The proximal end of the guidewire 128 may then be manually held to maintain the position of the guidewire within the patient's vasculature, while the delivery system is advanced over the guidewire and through the patient's vascular system. The function of the elastic cone 114 is to facilitate the advancement of the delivery system. By tucking the distal end of sheath 102 within the cone 114 as shown in FIG. 1F, the delivery system has a profile suited for successfully maneuvering about the sharp turns and angles of the patient's vasculature. The advancement of the delivery system continues until the distal ends of the catheter and sheath extend adjacent to or across the treatment site.

Next, the manipulator 140 on the proximal end of the delivery system is actuated by rotating the cap 146 on the proximal end of the housing 142 to move the sheath 102 proximally with respect to the catheter 104. In one embodiment, the proximal movement of the sheath 102 relative to the catheter 104 exposes and expands the device 110. The elastic cone 114 thereby disengages the sheath 102 and collapses in engagement about the distal portion of the catheter 104 as shown in FIG. 1.

When the device is properly placed at the treatment site, the device 110 is expanded or allowed to be self-expanded, as will be described in further detail hereinafter. FIG. 1G shows a device 110 expanded to engage the vessel wall. An agent can then be delivered to the lumen wall (e.g., via elution).

As discussed above, a guidewire 128 is provided within the intravascular catheter 104 to facilitate maneuvering the delivery system 100 within a patient's body lumen. As illustrated herein or previously, the guidewire system is a rapid-exchange type of guiding system. It will be appreciated, however, that other types, such as over-the-wire type systems, known in the art, can also be used. In one embodiment, the guidewire 128 is maneuvered to the treatment site first and the catheter assembly 100 is tracked over the guidewire 128 previously placed at the treatment site. The intravascular catheter 104 may be configured with a guidewire lumen as previously described therein for slidably advancing over the guidewire 128. A portion of the guidewire 128 and the delivery sheath 102 typically extend outside of the patient during a procedure.

The catheter delivery system 100 may be delivered to a vessel as a low profile system. In such an embodiment, the device 110 is in a collapsed, unexpanded, or compressed state. The delivery sheath 102 and/or catheter 104 constrain the device 110 in its collapsed, unexpanded or compressed state for the delivery.

At the treatment site, the device 110 is expanded as the delivery sheath 102 is proximally retracted in accordance with one embodiment of the invention. Other methods for expanding the device 110 may also be used. The device 110 may be deployed by the manipulation of the proximal handle or manipulator 140. For example, the housing 142 of the manipulator 140 can be held in the palm of the physician's hand, with the thumb and index finger thereof used to rotate cap 146 and thereby cause the necessary relative motion between the sheath 102 and intravascular catheter 104 to expose the device. Retracting the sheath 102 relative to the intravascular catheter 104 exposes the device in some embodiments. It is to be appreciated that other known manipulators can also be used to deploy the device. Upon completion of the treatment, the manipulator 140 can again be actuated by the physician rotating cap 146 with the fingers of the hand holding the manipulator 140, to cause relative rotation between the intravascular catheter 104 and the sheath 102, to pull the intravascular catheter 104 back into the distal end of the sheath 102 (or pushing the distal end of the sheath over the distal end of the intravascular catheter 104, depending upon the perspective). The entire assembly, including the device and the guidewire 128, can then be removed from the patient.

The device 110 is expandable with minimal force and does not expand with a great pressure that may cause damage to the lumen that is deployed within. As used in some embodiments of the present invention, the device 110 is also re-compressible or re-collapsible to allow it to be removed from the treatment site. The device 110 is thus configured so that it can be refracted into the delivery system 100 and removed from the patient.

The delivery sheath, and, in some embodiments, the catheter 104 should have sufficient elasticity to resist the outward bias of the device. The proper size and wall thickness of the delivery sheath 102 can be selected to provide such sufficient elasticity. The material of the delivery sheath 102 can also be chosen from the type of elastic material that has sufficient resilience to resist the expansive forces of the device held therein. Suitable materials used for the delivery sheath 102 are available and known in the art.

The catheter body can be formed by conventional techniques, for example by extruding and necking materials already found in intravascular catheters such as polyethylene, polyvinyl chloride, polyesters, polyamides, polyurethanes and composite materials. The various components may be joined using conventional bonding methods such as by fusion bonding or use of adhesives. Lumens can be formed in the tubular member using techniques known in the art, such as, for example, extrusion. The tubular members may have a wall made to comprise supporting braids or structures that provide flexibility while preventing crushing or kinking as the catheter is maneuvered to the site.

As discussed above, the device is configured to deliver an agent or combinations of agents to a vessel. In one embodiment, the agent(s) may be delivered to the vessel via elution, as described in greater detail hereinafter. Other methods for delivering agents may additionally or alternatively be used to deliver the agent(s). Elution may occur due to hydrostatic pressures and/or the drug concentration gradient.

A variety of suitable agents can include therapeutic and diagnostic agents. The agents are typically intended for treatment and/or diagnosis of coronary, neurovascular, and/or other vascular disease, and may be useful as a primary treatment of the diseased vessel, or alternatively, as a secondary treatment in conjunction with other interventional therapies such as angioplasty or stent delivery. The agent(s) may be eluted into the wall of an artery or any other cylindrically shaped structure, such as, for example, an artery, vein, ureter, bronchus, esophagus, intestine, vascular or dialysis graft, and the like.

Suitable therapeutic agents include, but are not limited to, antithrombolytic drugs, thrombolytic drugs, anti-inflammatory drugs, anti-proliferative drugs, anti-restenotic drugs, anti-inflammatory drugs, antibiotics, drugs restoring and/or preserving endothelial function, pro-healing, and the like. A variety of biologically active agents can also be used including, but not limited to, peptides, proteins, oligonucleotides, cells, siRNA, anisense, HDL mimetic, and the like. A variety of other diagnostic agents or agents that facilitate diagnosis using imaging (X-ray, CT, MR, PET, IVUS, OCT, conventional ultrasound, etc.) not mentioned herein can of course be used according to the present invention.

According to the present invention, agents described herein may be provided in a variety of suitable formulations and carriers including liposomes, polymerosomes, nanoparticles, microparticles, lipid/polymer micelles, and complexes of agents with lipid and/or polymers, and the like. As will be described hereinafter, the agents may be delivered to the vessel, in some embodiments, using a membrane. In one embodiment, the membrane may include nanoparticles or microspheres that contain the agent(s). The agent may be delivered to the vessel, alternatively or additionally, via infusion.

Accordingly, in some embodiments, one or more injection ports 162 can be provided and connected to the proximal handle 112. A conventional syringe 164 may be connected to the injection port 162 so as to communicate a fluid into the port. The injection port 162 can be use to communicate an agent or drug into a port and/or lumen in the device 110 to deliver the agent or drug at the treatment site, as will be described hereinafter.

Figure 2B:
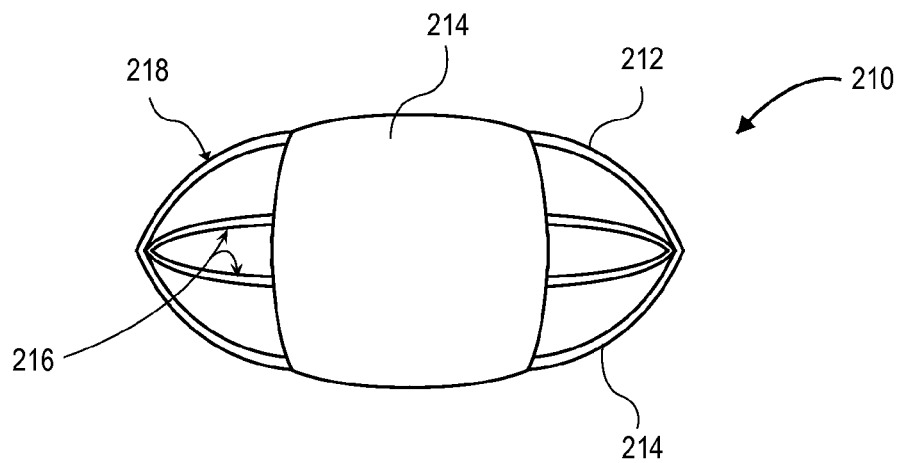

FIGS. 2A and 2B show a device 210 configured to deliver an agent to a vessel in accordance with one embodiment of the invention. The device is shown in a collapsed state in FIG. 2A and in an expanded state in FIG. 2B. The device 210 includes a frame 212 and a membrane 214.

The frame 212 is expandable to engage a vessel wall at a treatment site. In one embodiment, the frame 212 includes one or more wire loops that can expand and collapse. In FIGS. 2A and 2B, the device 210 includes two wire loops 216, 218. However, the frame 212 may include fewer than two loops or more than two loops. The frame 212 is typically configured to radially expand to meet the inner diameter of a target vessel. For example, the frame 212 is configured to have an expanded diameter of about 2 to about 5 mm for a coronary artery. In one embodiment, the frame 212 is designed such that the same size device 210 can perform agent delivery to a variety of different sized vessels, due to the elasticity of the expansion of the frame 212 into contact with an inner surface of a vessel wall. The frame is typically formed of a super-elastic or shape memory alloy or other self-deploying material, such as, for example, a nickel-titanium (NiTi) alloy (e.g., nitinol). Alternatively, stainless steel or other biocompatible metals or polymers can be utilized to form the frame 212.

In one embodiment, the wire loops 216, 218 are part of a guidewire. For example, a portion of the guidewire 128, described above with reference to FIGS. 1A-1G, may be the frame 212 of the device 210. In one embodiment, a distal portion of the guidewire is modified to form the wire loops 216, 218. For example, slits may be formed in the distal portion of the guidewire. It will be appreciated that other processes for forming the wire loops are contemplated. The membrane 214 can be secured to the guidewire over the modified distal portion.

The membrane 214 protects the luminal surface of the vessel from elevated shear stresses that occur during the rapid infusion of fluids, such as occurs during hemodialysis. The membrane also serves as a carrier of agents that are eluted from the membrane 214 into the arterial wall while the membrane 214 is in contact with the luminal surface of the artery (or other treatment site).

The membrane 214 is shown attached to an outer surface of the frame 212. In one embodiment, the membrane 214 is centrally located between the ends of the frame 212. The membrane typically has a length about equal to the length of the central working length section of the frame 212. It will be appreciated that the membrane 214 can be shorter or larger than the membrane shown in FIGS. 2A and 2B. The sleeve can be formed of a variety of suitable polymeric materials, including, for example, ePTFE. In one embodiment, the membrane 214 is impermeable.

Figure 3A:
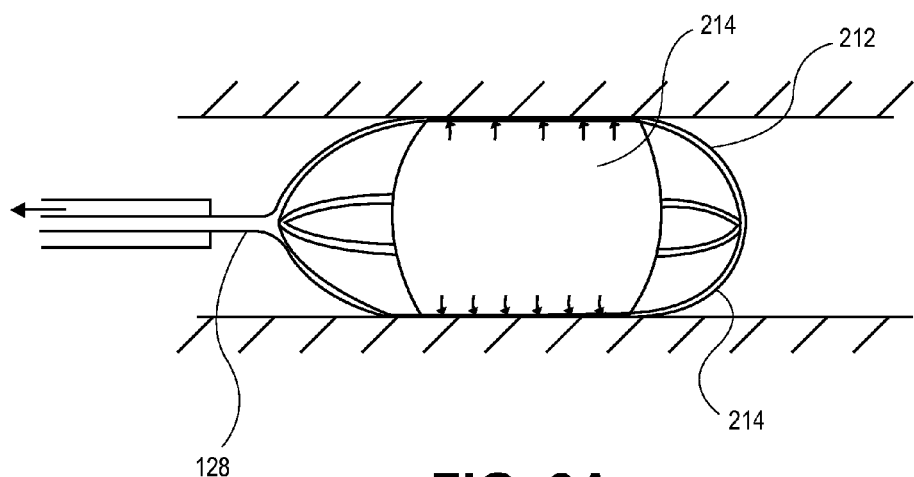
FIGS. 3A-3B are schematic drawings of delivery of the elution device of FIGS. 2A-2B at a treatment site in accordance with one embodiment of the invention.
Figure 3B:
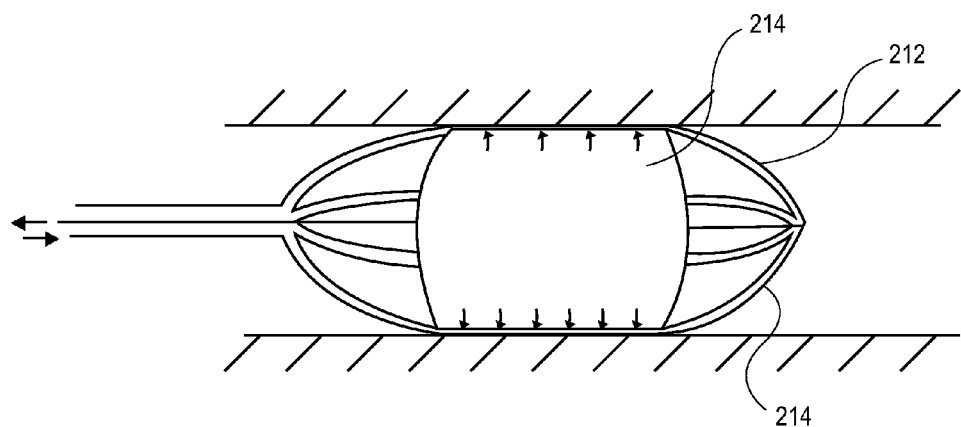

FIGS. 3A-3B show delivery of the device 210 at a treatment site. As shown in FIGS. 3A-B, at least a portion of the wire loops 216, 218 make contact with the arterial wall when the frame 212 is expanded. When the frame is collapsed 212, the device 210 can pass through catheter lumens and/or needles. FIG. 3A illustrates a self-expanding device in which axial movement of the catheter (or needle or sheath) relative to the guidewire allows the frame 212 to expand. FIG. 3B illustrates an actively expanded device in which an axial manipulation of a distal end of the frame 212 relative to a proximal end of the frame 212 expands the frame 212.

FIGS. 4A-4F show a device 310 configured to deliver an agent in accordance with one embodiment of the invention. The device 310 includes a structure 312 and at least one membrane 314. In one embodiment, the structure 312 is a self-expanding retractable structure. The self-expanding retractable structure may be similar to an embolic protection device and/or a stent-like structure, as known in the art. The structure 312 may be formed of a super-elastic or shape memory alloy or other self-deploying material, such as, for example, nitinol. Alternatively, stainless steel or other biocompatible metals or polymers can be utilized to form the structure 312.

The membrane 314 may be an impermeable membrane. In one embodiment, the membrane 314 is impermeable to the agent(s). In some embodiments, a second membrane 316 is provided (see FIG. 4D). The second membrane 316 is positioned external to the membrane 314. In one embodiment, the second membrane 316 is a porous membrane. In one embodiment, the second membrane 316 is substantially more permeable to the agent(s) than membrane 314. The second membrane 316 may be used to deliver the agent(s) to the vessel.

Figure 4A:
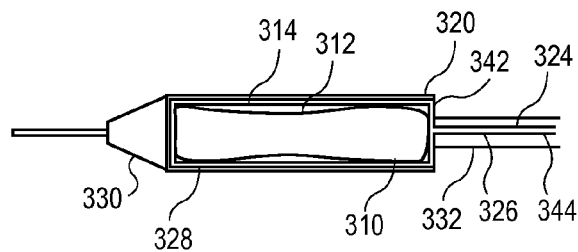
FIGS. 4A-4E are side views of an elution device in accordance with one embodiment of the invention.

FIG. 4A shows the device 310 in a catheter assembly 320. In one embodiment, the catheter 320 is the catheter assembly 100 described above with respect to FIGS. 1A-1G. It will be appreciated that other catheter assemblies may be used. The catheter 320 includes a guidewire lumen 324 and a guidewire 326 slideably engaged in the guidewire lumen 324. FIG. 4A shows the device 310 in an undeployed state. Catheter 320 has a moveable outer sheath 328, which is shown in its most distal position and may butt up against an atraumatic tip 330.

Figure 4B:
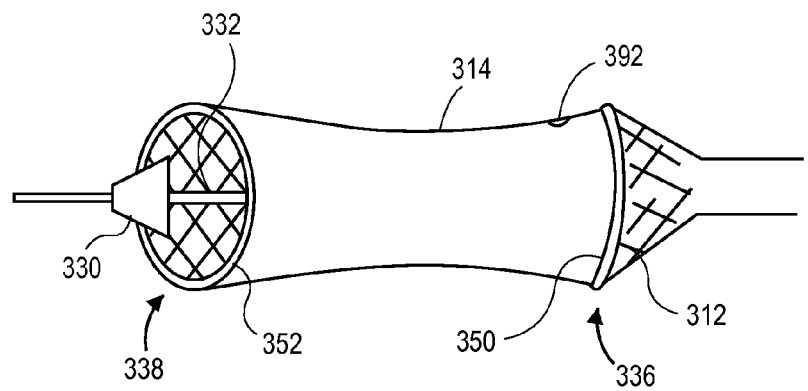

FIG. 4B shows the device 310 in its deployed state. In its deployed state, the outer sheath 328 is withdrawn proximally relative to an inner member 332. This withdrawal uncovers the device 310, which expands into contact with the walls of vessel 334. The proximal end 336 of the self-expanding retractable structure 310, is attached to the inner member 332 and may be configured similar to that of, for example, a conventional NiTi self-expanding stent or like that of the proximal end of a conventional embolic protection device. In such a configuration, when deployed, blood may flow through the proximal end 336 of the self-expanding retractable structure 310. The distal end 338 of the self-expanding retractable structure 310 is also open. Thus, blood flow may through self-expanding retractable structure 310 when it is deployed.

In some embodiments (not shown), the distal end of the self-expanding retractable structure 310 may also be attached to the inner member 332 using similar configurations as that described for proximal end 336. Such embodiments may be preferred, as they may minimize any relative motion between the self-expanding retractable structure 310 and the walls of the vessel 334 during deployment or retraction of the self-expanding retractable structure 310.

In one embodiment, inner member 332 also contains an infusion lumen 342 which transitions to an infusion tube 344. The distal end 346 of the infusion tube 344 is attached and sealed to the self-expanding stent-like structure 312 and the membrane 314 such that the infusion lumen 342 communicates with an outer portion of the membrane 314 (i.e., external to the device 310). Thus, any agent(s) infused through the infusion lumen 342 will empty out between the wall of the vessel 334 and the membrane 314, as described in further detail hereinafter.

In one embodiment, an agent(s) may be applied, coated and be a component of a coating applied on at least a portion of the OD surface of membrane 314. When catheter 320 is being positioned in the vessel, sheath 328 covers membrane 314, limiting the amount of the agent that elutes into the bloodstream and is lost systemically. When catheter 320 is positioned as desired, the sheath 328 is withdrawn and the structure 310 expands to position the agent on membrane 314 between the vessel wall and the membrane 314.

Figure 4C:
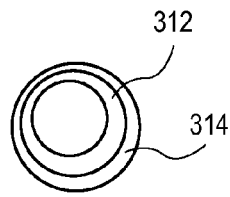
Figure 4D:
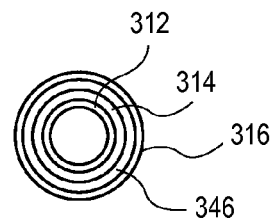
Figure 4E:
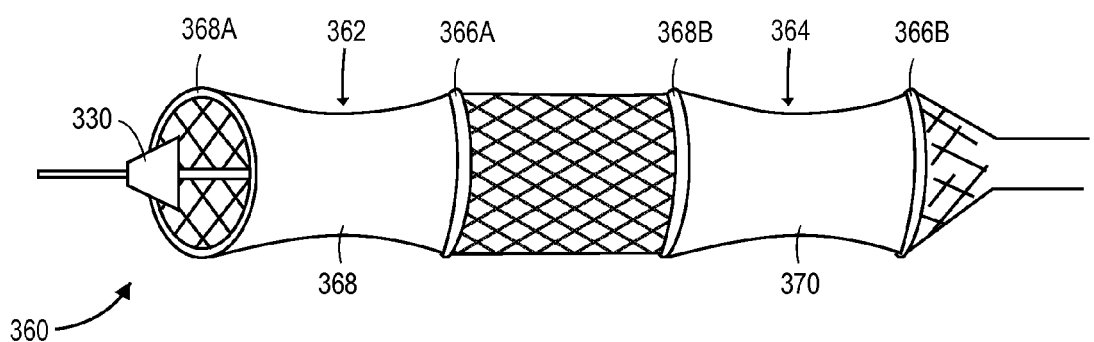

As shown in FIG. 4E, in one embodiment, the device 310 includes two membranes: a first membrane 314 and a second membrane 316. In one embodiment, the first membrane 314 is an impermeable membrane, and is positioned to be exposed to the vessel lumen. In one embodiment, the second membrane 316 is a porous membrane, and is positioned to be exposed to the vessel wall. Both membranes 314 and 316 may be positioned both internal or external the structure 312. Alternatively, the second membrane 316 may be positioned external the structure, while the first membrane 314 is positioned internal the structure 312.

The membrane 314 may have an open-ended cylindrical shape. It will be appreciated that the membrane 314 may refer to a single membrane 314 as shown in FIG. 4D or a first membrane 314 and a second membrane 316 as shown in FIG. 4E. The membranes 314 and 316 are attached to the structure 312 and/or each other to form an enclosed space 346 between the membranes 314 and 316. In one embodiment, the infusion tube 344 is attached and sealed to the structure 312 and the membranes 314 and 316, such that the infusion lumen 342 communicates with the enclosed space 346 between the two membranes 314 and 316. In one embodiment, an agent(s) may be applied, coated and be a component of a coating applied on at least a portion of the OD surface of membrane 314 and/or the ID surface of membrane 316.

The structure 312 may include a proximal seal 350 and a distal seal 352. Seals 350, 352 substantially reduce blood flow through the volume between the seals 350, 352, the vessel wall and membrane 314. As a result, seals 350, 352 substantially reduce the systemic loss of the agent(s) from this volume and allow the concentration of the agent(s) in this volume to be higher than if the agents(s) were washed away by normal blood flow. The seals 350, 352 may be proximal and distal rings that form part of the structure 312 by, for example, incorporating more metal (width, thickness and/or pattern) than other portions of the structure 312. Additionally or alternatively, the expanded diameter of the structure 312 at the proximal and distal ends may be greater than the expanded diameter at the central portions of the structure 312.

In one embodiment, the seals 350, 352 exert more pressure against the vessel wall than the central portions of the device 310 (i.e., between seals 350 and 352). In some embodiments, portions of the device 310 between the seals 350, 352 may not even contact the vessel wall. Thus, when an agent(s)/solution is infused into the infusion lumen 342 and into or outside of the structure 312 or a coated agent(s) elutes into the blood, the agent(s) may be substantially trapped between the structure 312 and the vessel wall between the two seals 350, 352. In some embodiments, the pressure of the infusion should be controlled to be below the pressure exerted by the seals 350, 352 against the vessel wall. In some embodiments, the pressure of the seals 350, 352 against the vessel wall are designed such that pressure of the infusion applied to the vessel wall is limited such that, should an excessive volume or pressure of the infusion be accidentally applied, the structure 312 at seals 350 and/or 352 will collapse and allow infusion flow out of the trapped area. Such a design may provide at least three safety effects. A first exemplary safety effect is the pressure applied to the vessel wall by the infusion is limited and thus, vessel wall damage due to infusion pressure or volume may be avoided or limited to acceptable levels. A second exemplary safety effect is the pressure applied to the structure 312 between the seals 350, 352 is thus also limited and thus, the amount of collapse of this portion of the structure 312 may be limited by design to avoid substantially occluding vessel blood flow and thus, avoid ischemia. A third exemplary safety effect is the pressure applied to the vessel wall by the seals 350, 352 are limited by design to pressures that avoid or limit vessel wall damage to acceptable levels.

FIG. 4C illustrates a device 360 configured to deliver an agent proximal and distal a side branch in a vessel. The device 360 includes a first treatment section 362, a second treatment section 364 and an intermediate section 366 between the first and second treatment sections 362, 364. The first treatment section 362 and second treatment section 364 each include a membrane 368 and 370, respectively, while the intermediate section does not include a membrane. In addition, each treatment section 362, 364 each includes a proximal seal 366a, 366b and a distal seal 368a, 368b. By positioning the intermediate section at the side branch, blood flow in the side branch may be maintained when the device 360 is deployed.

The atraumatic tip 330, the device 310 (or 360) and/or the inner member 332 may contain radiopaque markers (not shown) to aid in positioning the catheter 320 and/or the device 310 (or 360), such that the agent is applied to the vessel wall as desired. Blood flow can be also be maintained through the vessel, and in some embodiments, in vessel side branches.

The device 310 (or 360), which may be mounted on a shaft (guidewire or catheter body), is positioned in the vessel and delivered to the treatment site in the retracted (collapsed) state, as described above with reference to FIGS. 1A-1G. When deployed (expanded) in the vessel, the proximal and distal portions (e.g., proximal and distal seals 350, 352) of the device 310 (or 360) are designed to apply a greater pressure to the vessel wall than the central portion of the device to form a seal with the vessel wall at the proximal and distal ends of the covered portion(s) of the device. The device 310 (or 360) may be deployed by, for example, retracting a sheath or advancing/retracting a wire or shaft, as discussed above. During deployment, as the structure expands into contact with the vessel wall, the blood between the membrane and the vessel wall may be forced out of the space between the membrane and the vessel wall by the sequential expansion nature of the device.

Figure 5A:
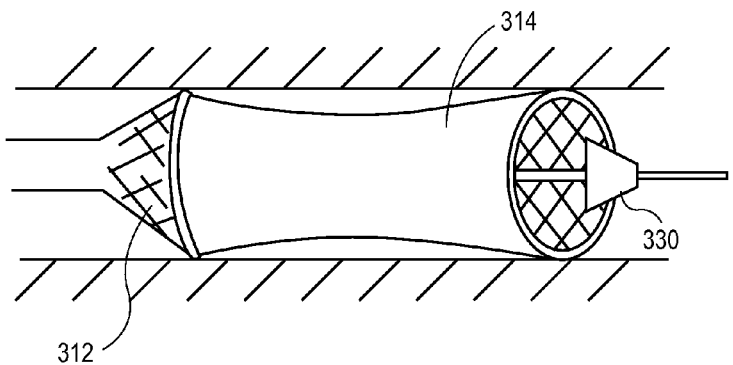
FIGS. 5A-5C are schematic drawings of delivery of the elution device of FIGS. 4A-4E at a treatment site in accordance with one embodiment of the invention.
Figure 5B:
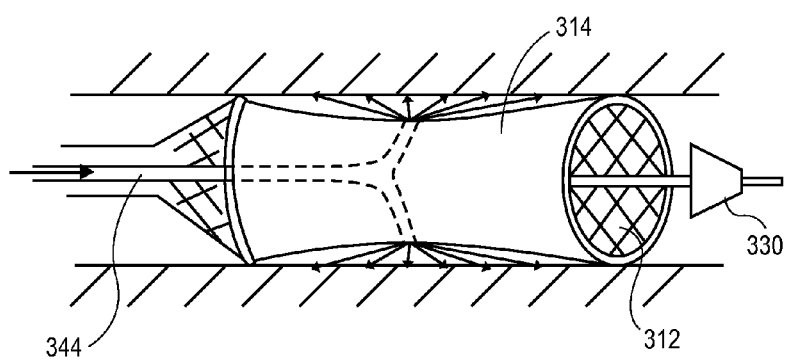
Figure 5C:
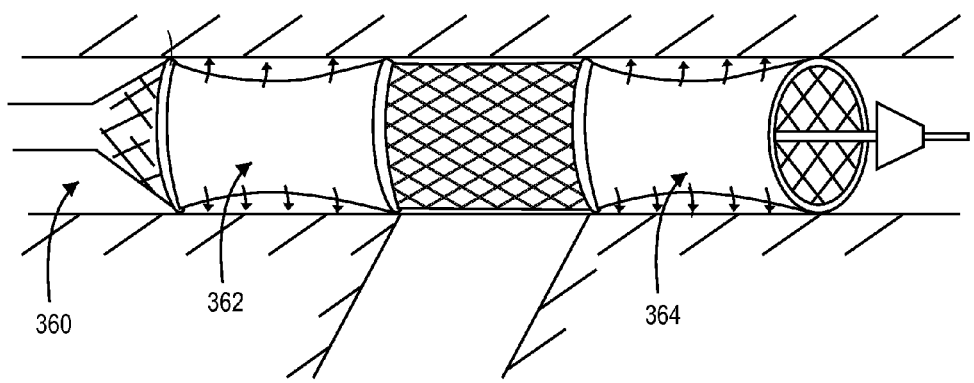

With reference to FIG. 5B, in one embodiment, the agent(s) may be infused via the infusion tube 344 into the central portion of the covered portion of the structure at a greater pressure than the local blood pressure, but less than the pressure required to cause flow of the agent past the seals 350, 352. Thus, the agent(s) may be applied directly to the vessel wall between the seals with minimal dilution by the blood for an extended period of time at a controlled (or designed maximum) pressure. After the desired exposure time, the pressure in the tube is lowered below local blood pressure and the agent(s) is withdrawn from the space between the membrane and the vessel wall (or in some embodiments, from between the membranes). Because the volume between the seals 350, 352, the vessel wall and membrane 314 is small, very little of the agent(s) can be washed away by the blood into the systemic circulation. After the agent(s) has been withdrawn, the outer sheath 328 may be advanced to collapse the device 310 (or 360). The device 310 (or 360) may then be repositioned to apply the agent(s) to another vessel or portion of the vessel wall, or be withdrawn from the patient. It will be appreciated that, in other embodiments, the membrane 314 and/or membrane 316 may carry the agent to the treatment site and, in some embodiments, the small volume between the seals 350, 352, the vessel wall and membrane 314 limit the amount of agent(s) that may be lost systemically.

Because the proximal and distal ends of the device 310 are not covered, blood flow in the vessel is only mildly obstructed when the device is deployed. Thus, ischemia is not an issue and the device 310 may remain deployed for an extended period of time to extend the agent exposure time, if desired. The device 310 may also be deployed and retracted much more rapidly and easily than balloon designs with similar agent application features, allowing more precise control of the agent exposure time and improved ease of use. The low profile of the device 310 also results in it being able to be used in smaller vessels and to allow greater blood flow than perfusion/porous balloon catheter designs with similar agent application features. The device can treat a wider range of vessel sizes than a perfusion/porous balloon catheter design with similar agent application features.

FIGS. 6A-6E show a device 410 configured to deliver an agent in accordance with one embodiment of the invention. The device 410 includes a central sleeve 412 and tubular members 414, 416 and 418. The central sleeve 412 is in fluid communication with the tubular members 414, 416, 418. Three tubular members are shown in FIGS. 6A-6E; however, it will be appreciated that fewer than three or greater than three tubular members may be used. One side of the tubular members 414, 416, 418 may be made from or lined with an impermeable membrane, as shown in FIG. 6E, while another side is made from a porous membrane, as shown in FIG. 6D. In one embodiment, the tubular member is made entirely from a porous membrane, while another side is lined with an impermeable membrane. In one embodiment, both sides of the tubular member are porous. In another embodiment, both sides of tubular member 416 are porous, while only one side of tubular members 414, 418 is porous. The small holes or pores of the tubular members 414, 416, 418 are configured to bathe the vessel wall with the agent(s), as shown in FIG. 6D. The central sleeve 412 isolates the agent delivered from the tubular members 414, 416, 418 from the blood flow to enhance delivery efficiency.

The device 410 may also include an inflation lumen 420 in central sleeve 412, as shown in FIG. 6C. The inflation lumen 420 can be connected to a port in each tubular member to deliver an agent at a vessel. In FIG. 6A, the tubular members 414, 416, 418 are shown connected in series; it will be appreciated, however, that other arrangements are contemplated.

Figure 7:
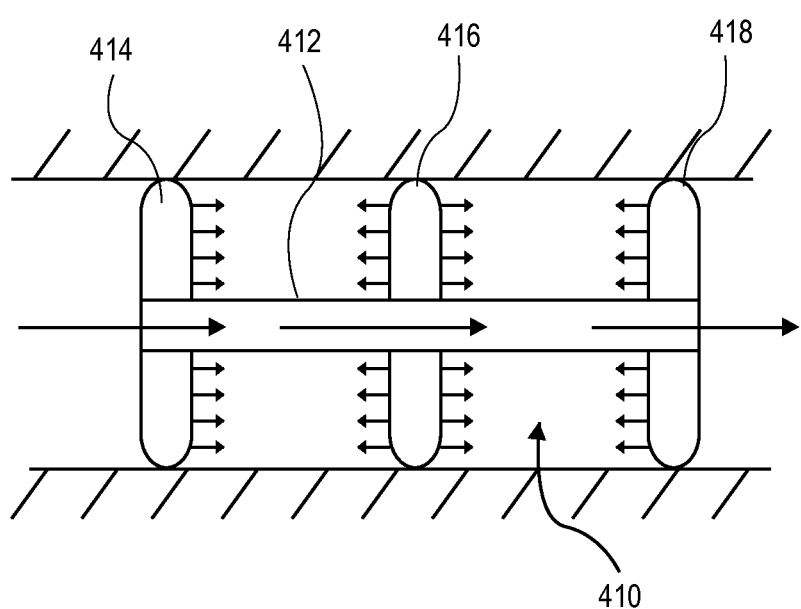
FIG. 7 is a schematic drawing of delivery of the elution device of FIGS. 6A-6F at a treatment site in accordance with one embodiment of the invention.

The device 410 may be delivered as described above with reference to FIGS. 1A-1G. The device 410 may be self-expanding or actively expanded, as described above. In one embodiment, the device 410 may be inflatable. FIG. 8 illustrates delivery of an agent to the vessel in accordance with one embodiment of the invention. As shown in FIG. 7, the device 410 allows the agent to be compartmentalized. The agent is restrained between the tubular members 414, 416 and 418. Blood can flow through the central sleeve 412, without interacting with the agent. Runoff into side branches does not prevent adjacent compartments from holding drug against the wall. The design also minimizes the area of the vessel (and, in particular, the endothelium) that is denuded by contact with the balloon.

Figure 8A:
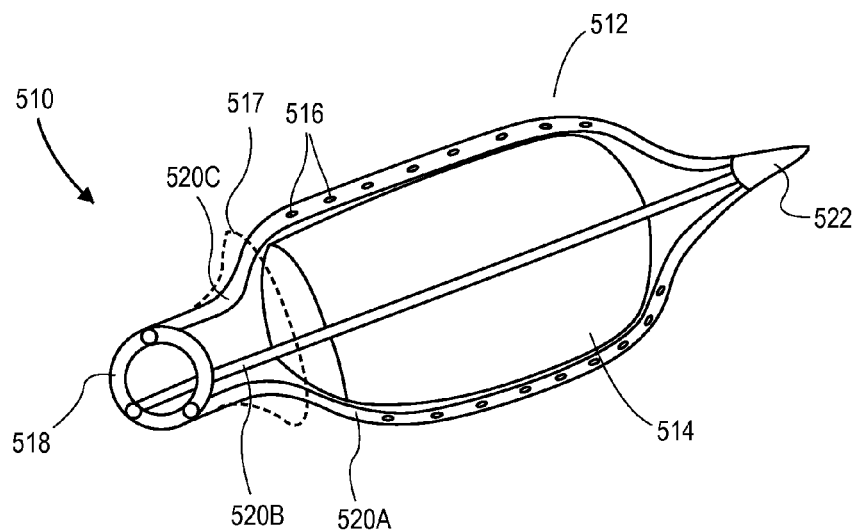
FIGS. 8A-8C are side views of an elution device in accordance with one embodiment of the invention.
Figure 8B:
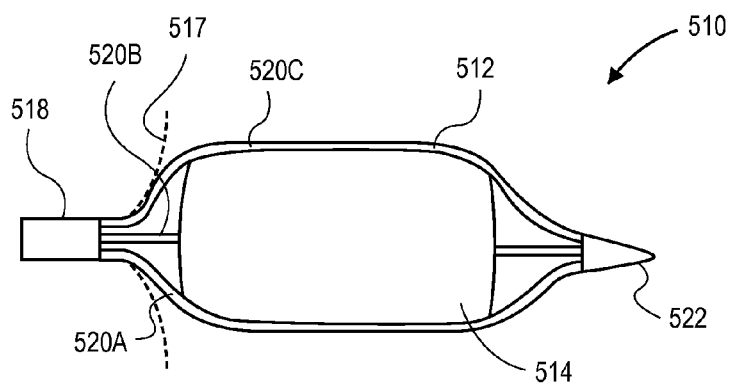
Figure 8C:
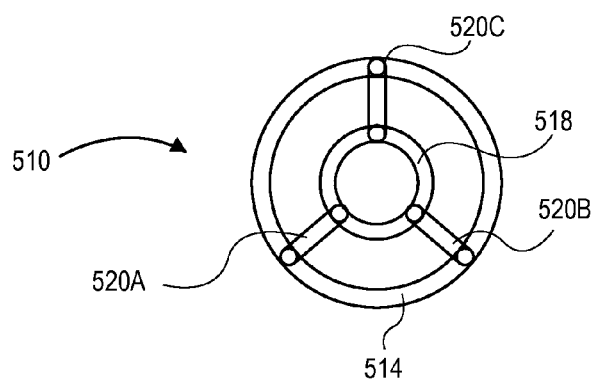

FIGS. 8A-C show a device 510 configured to deliver an agent in accordance with one embodiment of the invention. The device 510 includes a tubular cage 512 and a membrane 514. The membrane 514 is positioned internal the cage 512. The tubular cage 512 includes a plurality of openings 516 therein. The openings 516 are configured to deliver the agent(s) to the treatment site. In one embodiment, the openings are non-uniform. For example, the number and/or size of openings may be greater at a distal end of the device. In one embodiment, the tubular cage 512 is made from nitinol; it will be appreciated that other shape memory alloys may be used. Alternatively, other biocompatible metals or polymers may be used. In FIGS. 8A-8C, the tubular cage 512 includes three tubular members 520a, 520b and 520c; it will be appreciated that fewer than three or greater than three tubular members may be provided. The tubular members 520a-c are shown connected at an atraumatic tip 522.

The number of tubular members can be any number of tubular members, including two tubes to eight or more tubes. In one embodiment, three to five tubes is used for coronary vessels. The diameter of the tubular members can also vary and can be any value or range of values between 0.010" and 0.025" or more. The diameters of the openings 516 can be tuned for appropriate agent flow volume and distribution. In one embodiment, the diameter of the openings may be smaller proximally to better distribute the agent(s). In one embodiment, the spacing between the openings 516 is varied.

The tubular members 520a-c of the cage 512 are in fluid communication with a manifold 518. The manifold 518 is in turn connected to a port outside the patient for introduction of the agent(s), as described above with reference to FIGS. 1A-1G.

The membrane 514 isolates blood flow. In one embodiment, the membrane 514 is impermeable. The membrane 514 is open at proximal and distal ends of the device to allow blood to flow through the device. In one embodiment, the membrane 514 covers the working length of the cage 512.

The device 510 may also include a flap (not shown). The flap may be provided either proximally or distally. The flap further isolate the agent from blood flow by enclosing the space between the membrane and vessel wall.

Figure 9:
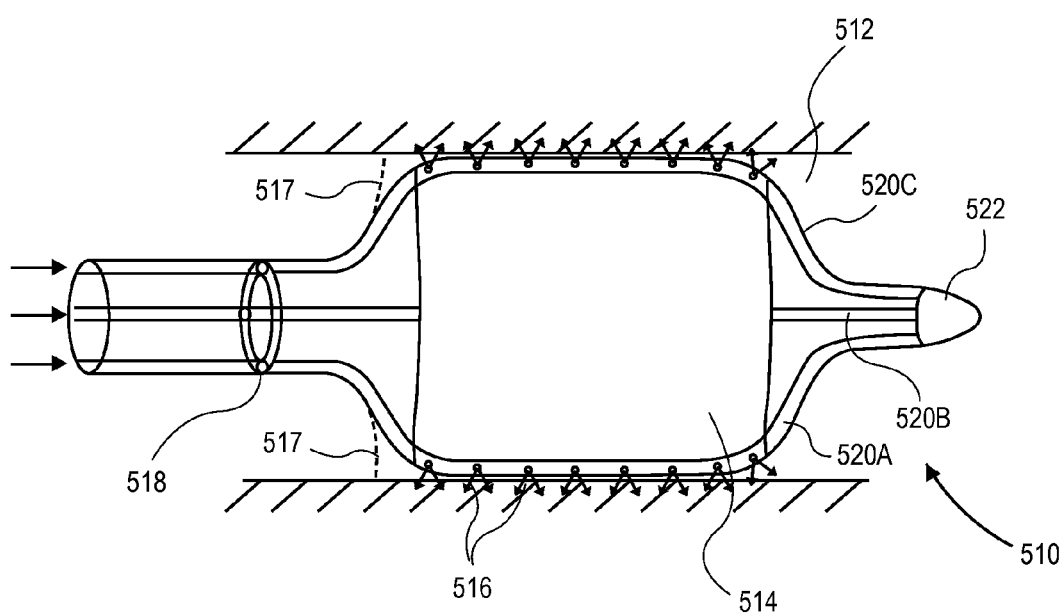
FIG. 9 is a schematic drawing of delivery of the elution device of FIGS. 8A-8C at a treatment site in accordance with one embodiment of the invention.

Deployment can be accomplished by a sheath if the device 510 is self-expanding, as described above with reference to FIGS. 1A-1G. The device 510 can also be deployed by pushing the manifold 518 distally while holding an inner member (not shown). As shown in FIG. 9, when the device 510 is expanded at the treatment site, the agent is delivered through the openings 516 in the tubular members 520a-c. The agent is delivered to the space between the membrane 514 and the vessel wall. In another embodiment, pushing the manifold expands the device. In another embodiment, delivery of the agent through the device expands the device. The size and/or number of openings can both regulate the expansion of the device and the flow of the agent through the device.

The device 510 can be used to deliver numerous drugs with minimal endothelial denundation and minimal, if any, ischemia during delivery. The tubular cage 512 reduces endothelial denundation, separating the agent(s) into compartments for enhanced delivery efficiency. The membrane 514 allows for blood flow during delivery of the agent(s).

Figure 10A:
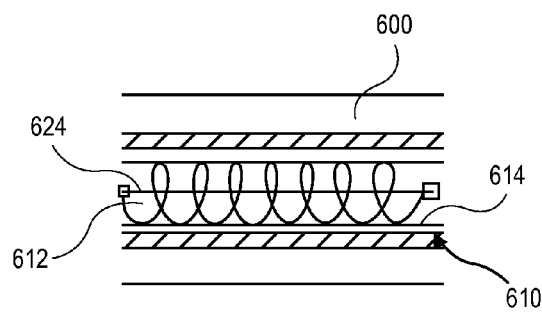
FIGS. 10A-10D are side views of an elution device in accordance with one embodiment of the invention.
Figure 10B:
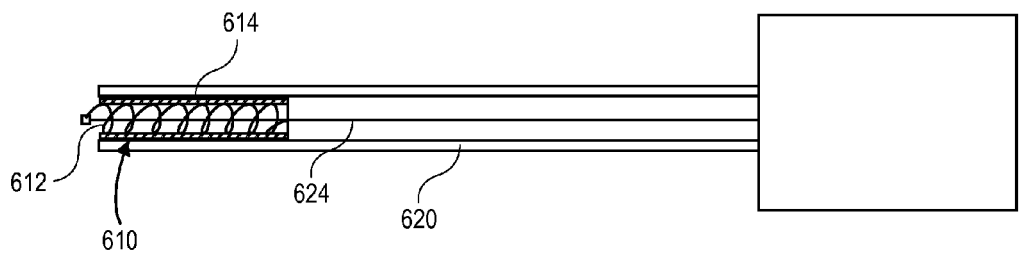
Figure 10C:
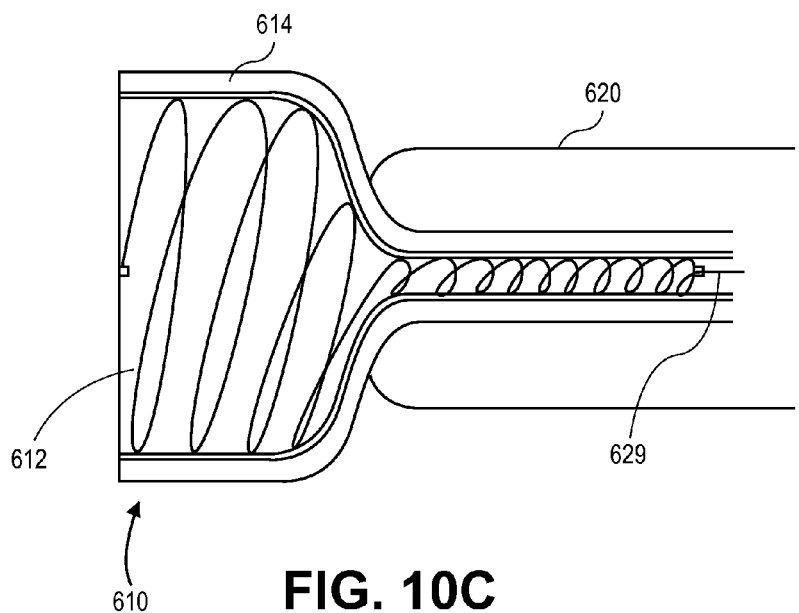
Figure 10D:
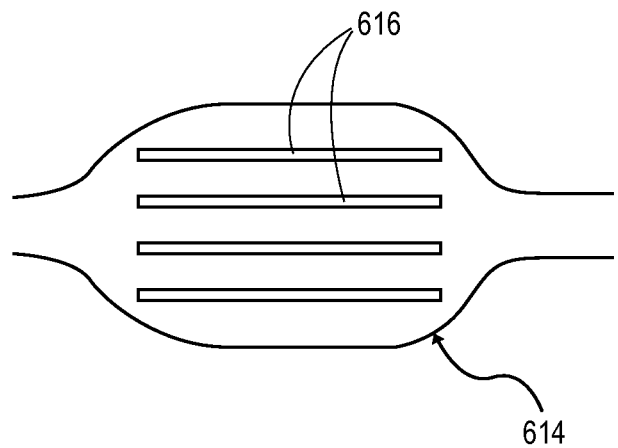

FIGS. 10A-D show a device 610 configured to deliver an agent in accordance with one embodiment of the invention. The device 610 includes a spring 612 and an elastic balloon 614. The elastic balloon 614 surrounds the spring 612. The elastomeric balloon 614 may be coated with a drug. In one embodiment, the balloon 614 is entirely covered with an agent. In another embodiment, the balloon 614 is covered with stripes of the agent, as shown in FIG. 10D. In one embodiment, the agent is provided in a gel, which is coated on the balloon 614. In one embodiment, the balloon 614 is a polymer. In one embodiment, the spring 612 is made from, for example, nitinol or other shape memory alloys.

A retractable sheath 620 may be provided over the device 610. The sheath 620 protects the agent on the balloon 614 and maintains pressure on the spring 612 to compress the spring 612 until the sheath 620 is retracted. In one embodiment, the sheath 620 is made from, for example, PTFE, so that the agent on the balloon 614 does not adhere to the sheath 620.

In another embodiment, as shown in FIG. 10B, the device 610 configured to deliver an agent includes the spring 612 and a catheter 626 configured to the deliver an agent. The drug may be directly applied or coated on the catheter 626. The sheath 620 covers the catheter 626 (as opposed to the balloon 614 in FIG. 10A).

Figure 11:
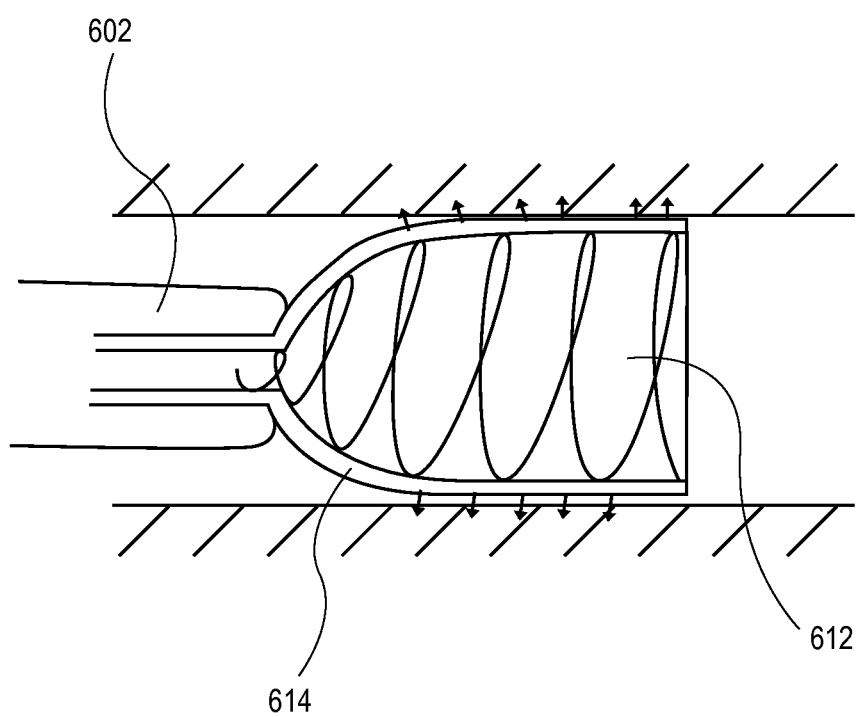
FIG. 11 is a schematic drawing of delivery of the elution device of FIGS. 10A-10D at a treatment site in accordance with one embodiment of the invention.

Refraction of the sheath 620 expands the spring 612. Expanding the spring 612, in turn, expands the balloon 614. The expansion of the spring 612 and the balloon 614 presses the agent on the balloon 614 against the vessel wall to deliver the agent to the treatment area, as shown in FIG. 11.

After treatment, the device 610 can be retracted. In one embodiment, the device 610 is simply pulled out (i.e., without compressing the device 610). In another embodiment, a straight mandrel 624 may be provided in the spring 612. The mandrel 624 is attached to the distal end of the spring. Rotating the spring 612 relative to the mandrel 624 expands or compresses the spring 612. The device 610 can then be refracted into the sheath 620.

The device 610 is advantageous because the spring expands and contracts to the contours of an individual's vasculature. In addition, the rate of sheath retraction controls the rate of drug application. The device 610 is also easier to manufacture than known balloon-based devices.

Following placement of a guiding catheter, angiography, any other diagnostic imaging, such as IVUS, the devices disclosed herein are introduced through the guiding catheter. Once the therapy portion of each of the devices is outside of the delivery system, the self-expanding properties of the devices cause the devices to expand. In some embodiments, flowing blood may further expand the devices and push the membrane covering the devices against the wall. Once the devices are against the wall, the agent(s) that have been placed on the outer surface of the membrane will diffuse out and then diffuse into the arterial wall or the agent is infused at the delivery site, as disclosed above. Since blood flow is not obstructed, the devices can be left in place for a sufficient time to allow a sufficient amount of the agent to diffuse out and into the vessel wall. The duration depends upon the drug, its release kinetics and its diffusion kinetics into and through the tissue(s). Upon completion of the drug delivery, the devices may be collapsed by retracting the devices into the delivery system or by advancing the delivery system over the device. In some embodiments, the collapsed device can then be removed and replaced with new or different devices if additional areas require therapy. In other embodiments, the collapsed device can then be re-positioned at another desired therapy site, the device allowed to expand and the treatment applied, as described above. After treatment of all desired sites, the device may be collapsed, as described above, and removed.

For vessel regional therapy and other applications, it is desirable to apply a concentrated form of the therapeutic agent to large sections of the vessel wall for a period of time at a higher pressure than the tissue to cause the therapeutic agent to move into the tissue in therapeutically significant concentrations and to limit the systemic exposure of the agent to move into the tissue in therapeutically significant concentrations and to limit the systemic exposure of the agent to the patient to avoid potential effects of the agent on other portions of the body. Blood flow washes infused agents away systematically in a short time and ischemia limits the time that blood flow can be stopped, especially in cardiac applications. To pressurize a vessel with an agent usually requires vessel occlusion, which limits the time that the vessel wall is exposed to the agent (ischemia) and when the occlusion is removed a significant quantity of the agent washes away systemically. The devices disclosed herein solve these problems and applies the therapeutic agent under controlled conditions to a known, relatively large portion of the vascular wall.

Advantages of the devices disclosed herein include drug delivery to the entire wall in contact with the device. The devices are not flow limiting. Drug delivery can be sustained for a considerable amount of time because blood flow is sustained. Delivery of the agent with a membrane provides a matrix into which or on which considerable amounts of the agent(s) can be stored. Minimal injury to the vessel wall results because the devices are deployed atraumatically. The devices can be easily re-positioned, removed and/or replaced with different or the same devices for treatment of an area proximal or distal to the previously treated area or another artery. The devices are also compatible with current guiding catheter systems.

In some embodiments, porous refers to a material is formed such that it has holes/gaps in its surface, allowing all or almost all portions of a solution to pass through. In some embodiments, permeable refers to material has a microstructure that selectively passes a portion of a solution; that is, portions of a solution may pass through the material structure at different rates.

The methods which are described and illustrated herein are not limited to the exact sequence of acts described, nor are they necessarily limited to the practice of all of the acts set forth. Other sequences of events or acts, or less than all of the events, or simultaneous occurrence of the events, may be utilized in practicing the embodiments of the present invention.

The foregoing description with attached drawings is only illustrative of possible embodiments of the described method and should only be construed as such. Other persons of ordinary skill in the art will realize that many other specific embodiments are possible that fall within the scope and spirit of the present idea. The scope of the invention is indicated by the following claims rather than by the foregoing description. Any and all modifications which come within the meaning and range of equivalency of the following claims are to be considered within their scope.

What is claimed is:

1. An agent delivery device comprising:
    an expandable device having a spring;
    a mandrel coupled to the spring;
    an elastic balloon surrounding the spring;
    an agent coating the balloon; and
    a retractable sheath surrounding the balloon and the expandable device having a retracted position and an unretracted position, wherein the spring expands when the sheath is in the retracted position and the agent is protected in the unretracted position,
    wherein rotating the spring relative to the mandrel expands or compresses the spring.

2. The device of claim 1, wherein the agent is selected from the group consisting of agents that inhibit intimal thickening, agents that inhibit pannus formation, agents that promote thrombus dissolution, thrombolytics, agents that inhibit local inflammation, agents that inhibit infection, anti-inflammatories, antibiotics, antirestenotics, and combinations thereof.

3. The device of claim 1, wherein a material of the spring comprises nitinol.

4. The device of claim 1, wherein the spring is retractable.

5. The device of claim 1, wherein the drug is coated on the elastic balloon in stripes.

* * * * *